(12) United States Patent
Prokhorov et al.

(10) Patent No.: US 10,772,835 B2
(45) Date of Patent: Sep. 15, 2020

(54) METHOD OF OBTAINING A PHARMACOLOGICALLY ACTIVE LIPOSOMAL CYTOCHROME C AND NITRIC OXIDE COMPLEX

(71) Applicant: Pylypenko Oleksandr, Kyiv (UA)

(72) Inventors: Vitalii V. Prokhorov, Kharkov (UA); Anatoliy I. Solovyov, Kyiv (UA); Oleksandr S. Khromov, Kyiv (UA)

(73) Assignee: Pylypenko Oleksandr, Kyiv (UA)

( * ) Notice: Subject to any disclaimer, the term of this patent is extended or adjusted under 35 U.S.C. 154(b) by 64 days.

(21) Appl. No.: 16/164,318

(22) Filed: Oct. 18, 2018

(65) Prior Publication Data
US 2019/0125673 A1    May 2, 2019

(30) Foreign Application Priority Data

Oct. 31, 2017   (UA) ............................. A201710558

(51) Int. Cl.
| | | |
|---|---|---|
| A61K 9/127 | (2006.01) | |
| A61K 38/41 | (2006.01) | |
| A61K 47/02 | (2006.01) | |
| A61K 47/69 | (2017.01) | |

(52) U.S. Cl.
CPC .......... *A61K 9/1277* (2013.01); *A61K 38/415* (2013.01); *A61K 47/02* (2013.01); *A61K 47/6911* (2017.08)

(58) Field of Classification Search
None
See application file for complete search history.

(56) References Cited

FOREIGN PATENT DOCUMENTS

| | | |
|---|---|---|
| CN | 101019836 A | 8/2007 |
| EA | 201201592 A1 | 6/2014 |
| EP | 3 158 990 A1 | 4/2017 |
| RU | 2110990 C1 | 5/1998 |
| UA | 44318 U | 9/2009 |

OTHER PUBLICATIONS

Osipov, A. N. et al., "The biological role nitrosyl complexes hemoprotein," *Advances of Biological Chemistry*, 2007, 47:259-292.
Vanin, A. F. et al., "The relationship between L-arginine-dependent nitric oxide synthesis, nitrite release and dinitrosyl-iron complex formation by activated macrophages," *Biochimica et Biophysica Acta (BBA)—Molecular Cell Research*, May 8, 1993, 1177(1):37-42, Elsevier B.V.
Vanin, A. F., "Endothelium-derived relaxing factor is a nitrosyl iron complex with thiol ligands," *FEBS Letters*, Sep. 1991, 289(1):1-3, Elsevier Science Publishers B.V.
Mulsch, A. et al., "The potent vasodilating and guanylyl cyclase activating dinitrosyl-iron(II) complex is stored in a protein-bound form in vascular tissue and is released by thiols," *FEBS Letters*, Dec. 1991, 294(3):252-256, Elsevier Science Publishers B.V.
Stone, J.R. et al., "Electron Paramagnetic Resonance Spectral Evidence for the Formation of a Pentacoordinate Nitrosyl-Heme Complex on Soluble Guanylate Cyclase," *Biochemical and Biophysical Research Communications*, Feb. 15, 1995, 207(2):572-577, Academic Press.
Frostell, C. et al., "A Selective Pulmonary Vasodilator Reversing Hypoxic Pulmonary Vasoconstriction," *Circulation*, Jun. 1991, 83(6):1-11, American Heart Association, Inc.
Gaston, B. et al., "Endogenous nitrogen oxides and bronchodilator S-nitrosothiols in human airways," *Proc. Natl. Acad. Sci.*, Dec. 1993, 90:10957-10961.
Culotta, E. et al., "No News Is Good News," *Science*, Dec. 18, 1992, 258:1862-1865.
Beckman, J. S. et al., "Apparent hydroxyl radical production by peroxynitrite: Implications for endothelial injury for nitric oxide and superoxide," *Proc. Nati. Acad. Sci.*, Feb. 1990, 87:1620-1624.
Bredt, D. S. et al., "Cloned and expressed nitric oxide synthase structurally resembles cytochrome P-450 reductase," *Nature*, Jun. 27, 1991, 351:714-718.
Stuehr, D. J. et al., "Spectral Characterization of Brain and Macrophage Nitric Oxide Synthases," *The Journal of Biological Chemistry*, Oct. 1992, 267(29):20547-20550, The American Society for Biochemistry and Molecular Biology, Inc.
Brown, G. C., "Nitric oxide inhibition of cytochrome oxidase and mitochondrial respiration: Implications for inflammatory, neurodegenerative and ischaemic pathologies," *Molecular and Cellular Biochemistry*, Sep. 1997, 174:189-192, Kluwer Academic Publishers.
Basu, S. et al., "A Novel Role for Cytochrome c: Efficient Catalysis of S-Nitrosothiol Formation," *Free Radic Biot Med.*, Jan. 15, 2010, 48(2):1-20.
Sharpe, M. A. et al., "Reactions of nitric oxide with mitochondrial cytochrome c: a novel mechanism for the formation of nitroxyl anion and peroxynitrite," *Biochem. J.*, 1998, 332:9-19.
Zhang, F. et al., "Nitric Oxide Donors Increase Blood Flow and Reduce Brain Damage in Focal Ischemia: Evidence that Nitric Oxide is Beneficial in the Early Stages of Cerebral Ischemia," *Journal of Cerebral Blood Flow and Metabolism*, Mar. 1994, 14(2):217-226, Raven Press, Ltd., New York.

*Primary Examiner* — Brian J Davis
(74) *Attorney, Agent, or Firm* — Saliwanchik, Lloyd & Eisenschenk

(57) ABSTRACT

The invention relates to pharmaceutical industry and discloses a method of obtaining a new pharmacologically active liposomal agent containing substances that exhibit specific pharmacological activity on peripheral vessels and cavernous bodies of a mammal. More particularly, the invention relates to a method of obtaining a pharmacologically active liposomal cytochrome c containing nitric oxide. The new liposomal agent acts as a donor of the key biologically active substance—nitric oxide (NO).
A method of obtaining a pharmacologically active liposomal cytochrome c and nitric oxide complex comprises the treatment of the liposomal cytochrome c emulsion with gaseous nitric oxide (NO) until liposomal cytochrome c is completely reconstituted and the addition of an S-nitroso compound to the liposomal cytochrome c emulsion.

15 Claims, 10 Drawing Sheets

METHOD OF OBTAINING A PHARMACOLOGICALLY ACTIVE LIPOSOMAL CYTOCHROME C AND NITRIC OXIDE COMPLEX

FIELD OF INVENTION

The invention relates to pharmaceutical industry and discloses a method of obtaining a new pharmacologically active liposomal agent containing substances that exhibit specific pharmacological activity on peripheral vessels and cavernous bodies of the mammalian body. More particularly, the invention relates to the method of obtaining a pharmacologically active liposomal cytochrome c containing nitric oxide. The new liposomal agent acts as a donor of the key biologically active substance—nitric oxide (NO).

BACKGROUND OF INVENTION

The interaction of heme-containing proteins and nitric oxide and regulatory functions of the latter in changing the activity of enzymes while interacting with them, as well as the biological role of nitrosyl complexes of hemoproteins as means of depositing nitric oxide are described, for example, in the article [1].

Dinitrosyl iron complexes (DNIC) are considered to be a relatively stable form of NO in cells. Thiol groups of proteins or low-molecular-weight thiols (e.g., cysteine or glutathione) are involved in the formation of these complexes [2]. Such complexes are formed in macrophages and endothelial cells. They are considered as the main depot (pool) of NO in the body [3]. Experimental evidence suggest that NO can be released from endothelial cells in the form of dinitrosyl iron complexes (DNIC) rather than in an arbitrary form. Low-molecular-weight mercaptans (e.g., cysteine or glutathione) are known to compete with thiol groups of proteins for the formation of nitrosyl complexes. Finally, the profile of properties of dinitrosyl iron-sulfur complexes is characterized by the fact that they have practically the same physiological activity and stability as endothelium-derived relaxing factor (EDRF) and, therefore, can be involved in the biological action of NO [4]. NO is able to alter the activity of enzymes by interacting with their functionally important groups and, primarily, with heme iron (Fe-heme) and thiols. The activation of guanylate cyclase is the most striking example of this. Binding of NO to heme iron of the regulatory subunit of guanylate-cyclase causes a disruption in the bond between iron and nitrogen of a histidine imidazole group resulting in changes in both the structure of the active center and protein conformation [5]. The activity of enzyme increases tenfold leading to an increase in the level of cyclic guanosine monophosphate (cGMP). If platelets are target cells, then increasing cGMP causes a reduction in blood coagulation. In case of a smooth muscle cell, an increase in intracellular cGMP leads to a relaxation of smooth muscle. This mechanism underlies physiological phenomena, such as regulation of vascular tone, regulation of Oddi's sphincter tone in the duodenum and some other phenomena. As a regulator of vascular tone (and, in such way, of blood pressure), NO is involved in the pathogenesis of various cardiovascular diseases, including hypertension and atherosclerosis. NO is well known by its protective role at the initial stage of ischemia as a factor improving blood circulation and reducing tissue damage [6]. The ability of NO to affect the pulmonary blood flow and bronchial tone has been found to be therapeutic [7]. For example, S-nitrosoglutamate (a natural NO metabolite) regulates the air resistance of the bronchi [8]. As a neurotransmitter of the peripheral nervous system, NO provides reproductive functions in men and can play a crucial role in the treatment of impotence [9]. NO is involved in inflammatory and immune processes. Thus, macrophages activated by γ-interferon, tumor necrosis factors (TNF) and lipopolysaccharides (LPS) dramatically increase the synthesis of NO and ONOO—, damage bacterial cells and, in this way, provide antimicrobial action. At the same time, in case of sepsis, formation of NO in toxic quantities plays a negative role. Reduced vascular tone and inevitable fall in blood pressure under the action of NO can become critical and lead to shock. In case of ischemia/reoxygenation, increased synthesis of NO and ONOO—causes tissue damage and cell death [10]. NO toxicity at the cellular level is associated with the formation of nitrosyl complexes of heme proteins and/or their S-nitrosylation. The inhibition of enzymes of the respiratory chain, Krebs cycle, and DNA synthesis is a consequence of such modifications. Further, the development of oxidative stress, in the presence of NO, is associated with the production of a powerful oxidant—ONOO—which irreversibly suppresses enzymes and oxidizes lipids and DNA. Thus, on the one hand, NO can act as a pro-oxidant due to the formation of ONOO—. On the other hand, NO is an interceptor of free radicals and a reducing agent and, as such, may play the role of an antioxidant. NO readily reacts with other free radicals and thus can cause either an interruption in the lipid peroxidation chain or an inhibition of its initiation [11, 12]. In a number of pathophysiological processes occurring with the involvement of NO, nitrosyl complexes of heme-containing proteins can play an important role. This primarily refers to conditions associated with circulatory disorders—ischemia, hypertension, or shock—which are associated with the formation of nitrosyl complexes—guanylate-cyclase. A reduction in cellular respiration and increased production of free radicals by mitochondria in inflammatory and neurodegenerative processes may be associated with the formation of nitrosyl complexes of cytochromes of the electron transport chain [13].

The following analogues used for obtaining a pharmacologically active complex with nitric oxide are known to the applicant.

The prior art describes a composition for the release of nitric oxide (NO) which, if necessary, allows for the quick release of nitric oxide and, at the same time, the formation of S-nitrosothiol compounds [14]. The compound provides a slower release of NO and a longer duration of action. The composition comprises a liquid phase, containing a solvent and at least one reducing agent, and a solid phase, containing nitrate and/or nitrate, copper ions, and at least one thiol. Panteteine, alpha lipoic acid, phosphapantetheine, cysteine, homocysteine, thioglycolic acid, β-mercaptopropionic acid, β-mercaptoethanol, β-thioethanolamine, coenzyme A, cysteamide, γ-glutamylcysteine, phytogelatin, trypanothione, captopril, glutathione, and N-acetylcysteine are used as thiols suitable for the use in the said composition. The said composition can preferably be used in all clinical situations where the release of NO may affect the etiology and pathogenesis of a disorder. Particularly preferred is its use in the treatment of male sexual dysfunction, in particular erectile dysfunction.

The composition is produced by using a mixture formed by dissolving fumaric acid and ascorbic acid in propylene glycol and adding a solid phase, comprising a mixture of thiol (e.g., alpha-lipoic acid), sodium nitrite and powdered copper sulfate, to the solution followed by mixing at a room temperature. The resulting mixed solution contains propylene glycol, ascorbic acid, alpha-lipoic acid, fumaric acid, sodium nitrite, and copper sulfate residues. To use the described composition in this case, a special container is required to ensure the long-term separate storage of the liquid and the solid phase of the composition.

The release of nitric oxide (NO) and the use of thiol as a reducing agent is a common feature of the analogue and the present invention. However, the composition according to the analogue does not imply the use of hemocomplexes of liposomal cytochrome c which, in terms of its phospholipid composition, is biologically close to membrane cells of the mammalian body. A further drawback of the analogue is the use of two different phases of the composition and a special container for their storage.

The prior art discloses the use of phospholipids to produce a liposomal agent with nitric oxide (NO), where cytochrome c is used as a catalyst of nitrosylation reaction, i.e. conversion, where thiol (glutathione) is used as a substrate for nitrosylation [15]. The purpose of obtaining such a liposomal agent is to study catalytic properties of cytochrome c with nitric oxide. In the said reaction, activation of NO is achieved with a known prodrug of nitric oxide—V-PYRRO/NO, not with gas. According to [15], such agent is used only as a model close to the cell structure for purposes of research and not as a pharmacologically active agent. Nitrosothiols are also used as carriers and there is no use of cytochrome c and liposomes for this.

SUMMARY OF THE INVENTION

Embodiments of the invention obtain a stable pharmacologically active complex of liposomal cytochrome with nitric oxide (NO) from emulsion (a half product) containing cytochrome having the form of a liposomal agent (cytochrome c, incorporated in liposomes). After reconstitution with water to obtain an emulsion, the said lyophilizate exhibits the same activity at different stages of storage as a freshly prepared complex of liposomal cytochrome c and nitric oxide and maintains a stable size of liposomes, in particular no more than 300 nm.

Such is achieved by using a method of obtaining a pharmacologically active liposomal cytochrome c and nitric oxide complex that comprises the treatment of the liposomal cytochrome c emulsion with gaseous nitric oxide (NO) until liposomal cytochrome c is completely reconstituted and the addition of an S-nitroso compound to the liposomal cytochrome c emulsion.

According to one preferred embodiment, the liposomal cytochrome c emulsion may be treated by supplying gaseous nitric oxide (NO) using an inert carrier gas.

According to another preferred embodiment, argon may be used as an inert carrier gas.

According to yet another preferred embodiment, an inert carrier gas can be pre-filtered to a purity of at least 99.995%.

According to yet another preferred embodiment, an inert carrier gas may be purified after contact with gaseous nitric oxide (NO) from salt-forming admixtures of nitric oxide (NO).

According to yet another preferred embodiment, the liposomal cytochrome c emulsion obtained by high-pressure homogenization followed by lyophilic drying may be used.

According to yet another preferred embodiment, the liposomal cytochrome c emulsion reconstituted from the lyophilizate may be used. According to yet another preferred embodiment, liposomal cytochrome c having the form of emulsion may be pre-filtered using hydrophilic membranes before gaseous nitric oxide (NO) is supplied.

According to yet another preferred embodiment, prefiltration may be performed through at least two successively positioned hydrophilic membranes with a gradually decreasing pore diameter.

According to yet another preferred embodiment, liposomal cytochrome c having the form of emulsion may be treated with gaseous nitric oxide (NO) at a room temperature.

According to yet another preferred embodiment, the emulsion may be subject to extra filtration after the reconstitution of liposomal cytochrome. According to yet another preferred embodiment, after the filtration, the emulsion may be frozen at a temperature of minus 35° C. followed by lyophilic drying.

According to yet another preferred embodiment, S-nitrosothiol may be added to the emulsion to obtain S-nitrosothiol concentration in the range of 0.01 to 0.1 M in the emulsion.

According to yet another preferred embodiment, S-nitrosothiol may be added to the emulsion before the treatment with gaseous nitric oxide (NO) and/or during the treatment with gaseous nitric oxide (NO) and/or after the treatment with gaseous nitric oxide (NO).

According to yet another preferred embodiment, S-nitroso compound may be chosen from a group of S-nitrosothiols: nitroso-N-acetylpenicillamine, S-nitrosoglutathione (GS-NO), S-nitrosocysteine (Cys-no), and a mixture thereof.

There is the following causal relationship between the above-mentioned essential features of the invention and the technical result so achieved.

Being present in the preparation "Lipochrome, Lyophilizate for the Preparation of Emulsion for Injection" as an active substance, cytochrome c is a hemoproteide and interacts with nitric oxide with the help of iron-containing heme. Such reaction is possible only under certain conditions in the body (cells), specifically on the inner surface of mitochondrial membranes where cytochrome c is present. The emulsion (a half product) of the drug "Lipochrome, Lyophilizate for the Preparation of Emulsion for Injection" is cytochrome c incorporated in liposomes which, in terms of its phospholipid composition, is close to biological membranes of cells in the body. Thus, when the emulsion is treated, nitric oxide transforms liposomal cytochrome c into a reconstituted state by binding to its heme and forming a nitrosyl complex.

The studies show (Table 1) that liposomal cytochrome c reconstituted with nitric oxide is an unstable compound, because cytochrome c inherently tends to its energy-efficient state—the oxidized state. The cyt c3+-NO complex may inadvertently be destroyed in the presence of oxygen, and virtually all NO, which has passed into the external environment, turns into nitrite [16].

The use of an analogous product "Lipochrome, Lyophilizate for the Preparation of Emulsion for Injection" is described in reference sources [17-20].

TABLE 1

Parameters of stability of the liposomal cytochrome c emulsion after the treatment with nitric oxide (NO)

| Sample number | Time of treatment of the emulsion with nitric oxide, minutes | Time of storage of the emulsion at a room temperature, minutes | Emulsion color | Optical density ratio, 560/528 nm | pH | Size of liposomes, nm |
|---|---|---|---|---|---|---|
| Initial emulsion (a half product) | | | Light brown | 0.76 | 6.85 | 102.5 |
| 1 | 30 | 0 | Bright pink | 0.85 | 6.86 | 130.7 |
| 2 | 30 | 10 | Bright pink | 0.82 | 6.75 | 126.5 |
| 3 | 30 | 30 | Light pink | 0.8 | 6.73 | 143.4 |
| 4 | 30 | 60 | Light brown | 0.79 | 6.68 | 165.5 |
| 5 | 30 | 90 | Light brown | 0.77 | 6.6 | 178.3 |
| 6 | 45 | 0 | Bright pink | 0.87 | 6.83 | 135.6 |
| 7 | 45 | 10 | Bright pink | 0.85 | 6.75 | 140.1 |
| 8 | 45 | 30 | Light pink | 0.8 | 6.72 | 167.7 |
| 9 | 45 | 60 | Light brown | 0.76 | 6.65 | 170.5 |
| 9 | 45 | 90 | Light brown | 0.76 | 6.61 | 181.3 |

To obtain a stable liposomal cytochrome c and nitric oxide complex, nitroso compounds (as described above) are used; the latter are added in the emulsion at various stages to achieve concentrations in the range of 0.01 to 0.1 M in the emulsion. Following the filtration, the emulsion is subject to lyophilic drying. After reconstitution with water to obtain an emulsion, the resulting lyophilizate exhibits the same activity at different stages of storage as a freshly prepared liposomal cytochrome c and nitric oxide complex (Table 2) and retains the size of liposomes up to 300 nm.

TABLE 2

Activity of reconstituted lyophilizate obtained with the said method at various stages of storage and size of liposomes

| | Target product (examples 1, 2) | | | | | Target product (examples 3-6) | | | | |
|---|---|---|---|---|---|---|---|---|---|---|
| | 1 | 2 | 3 | 4 | 5 | 1 | 2 | 3 | 4 | 5 |
| Optical density ratio, 560/528 nm | 0.87 | 0.85 | 0.86 | 0.87 | 0.85 | 0.86 | 0.87 | 0.87 | 0.87 | 0.86 |
| Particle size, nm | 50.8 | 58.1 | 55.7 | 51.7 | 53.6 | 68.9 | 78.3 | 65.2 | 80.1 | 70.5 |

Examples 1-6 given in Table 2 will be described below.

DETAILED DESCRIPTION

Figure 1:
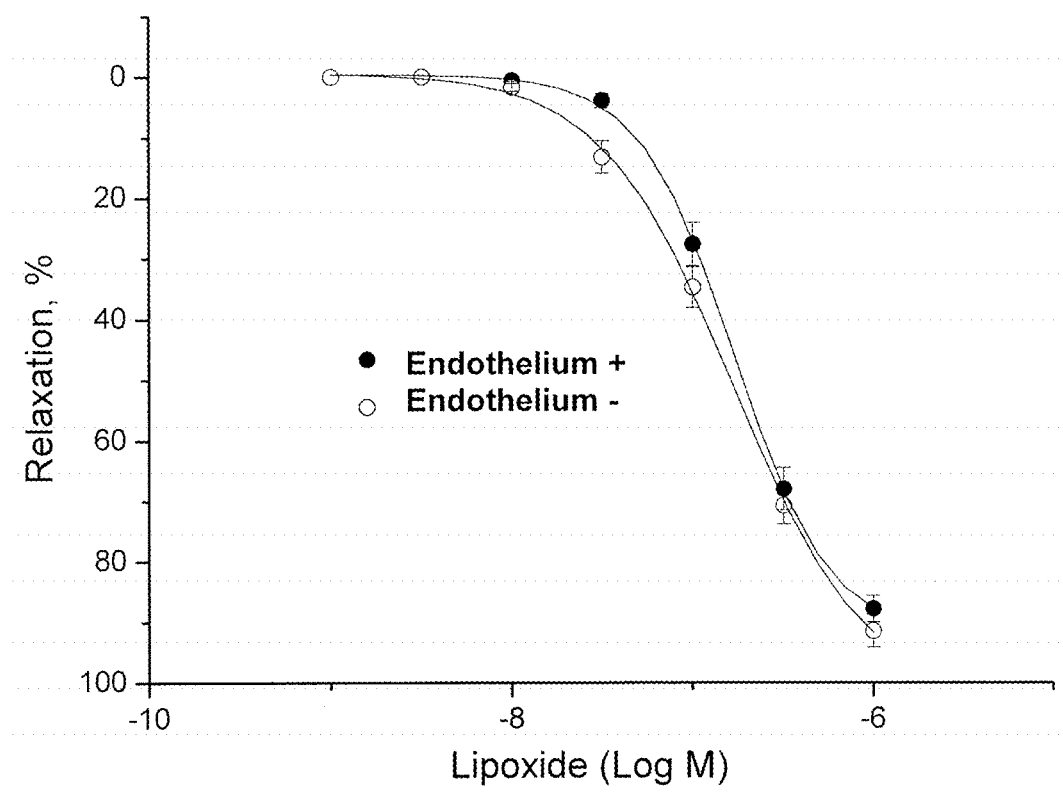
FIG. 1 is a diagram illustrating the contractile activity of intact and deendothelized rat thoracic aorta segments pre-activated by phenylephrine ($10^{-6}$ mol/l) exposed to a sample of the ex-tempore liposomal cytochrome c and nitric oxide complex (Lipoxide).

The invention will now be explained in greater detail with the reference to embodiments of the method of obtaining a pharmacologically active liposomal cytochrome c and nitric oxide complex and experimental data gathered as part of the study of target products and with the reference to the accompanying drawings.

The examples and figurative materials are in no way intended to limit the embodiments of the invention but to explain the essence of the invention and illustrate the possibility of achieving the claimed result.

The method according to the invention is implemented as follows.

The pharmacologically active liposomal cytochrome c and nitric oxide complex is obtained by S-nitrosylation of nitric oxide (NO) and nitroso compounds (nitrosothiols) of the protein cytochrome c, incorporated in the liposomal product "Lipochrome, Lyophilizate for Preparation of Emulsion for Injection", with purified gas. For S-nitrosylation, a semi-finished product (a half product) of the medicinal product "Lipochrome, Lyophilizate for Preparation of Emulsion for Injection" is used. It is an emulsion obtained by high-pressure homogenization followed by lyophilic drying. The emulsion is filtered successively through hydrophilic membranes with a pore diameter of 0.45 μm and 0.2 μm and then, at a room temperature, nitric oxide gas is passed through the emulsion pre-purified through aqueous sodium hydroxide solution 5 M to remove salt-forming admixtures of nitric oxide. Nitric oxide is supplied to the emulsion using an inert gas—high-purity argon (at least 99.995%). S-nitrosylation with nitric oxide is carried out until the emulsion changes its color from light brown to a stable bright pink. In this case, an absorbance spectrophotometer will show maxima at the wavelength of 528 nm and 560 nm. Such change in physical and chemical properties of the emulsion of the semi-finished product (half product) of the medicinal product "Lipochrome, Lyophilizate for Preparation of Emulsion for Injection" is associated with the addition of nitric oxide (NO) to the cytochrome c hemocomplex and its conversion into the reconstituted form.

S-nitrosothiols (Examples 3-6): S-nitroso-N-acetylpenicillamine (SNAP) (Examples 7-10), S-nitrosoglutathione (GS-NO) (Examples 1-6), and S-nitrosocysteine (Cys-NO) (Examples 11-14) are added to a semi-finished product (a half product) before and after the treatment with nitric oxide (NO) to obtain concentrations in the range of 0.01 to 0.1 M in the emulsion.

The emulsion is then re-filtered through hydrophilic membranes with a pore diameter of 0.45 μm and 0.2 μm, dosed in vials and is subject to lyophilic drying.

The following examples illustrate methods of obtaining a pharmacologically active liposomal cytochrome and nitric oxide (NO) complex (cyt c3+-NO) according to the invention and obtaining a stable form of the said complex.

EXAMPLE 1

An emulsion of a half-product of the medicinal product "Lipochrome, Lyophilizate for Preparation of Emulsion for Injection" is bubbled (purged) for 30 minutes with argon, an inert gas, pre-filtered through a hydrophobic filter with a pore diameter of 0.1 μm to remove atmospheric air. After bubbling of the emulsion, an argon supply line is switched to supply nitric oxide (NO) from a solution tank where metallic copper reacts with 30% nitric acid solution with the release of gaseous nitric oxide (NO). After the reaction vessel, argon, a carrier gas, passes through a vessel with a solution of 5 M sodium hydroxide to remove salt-forming admixtures of nitric oxide (NO) and enters a vessel with the emulsion. Treatment with nitric oxide (NO) is performed until complete reconstitution of liposomal cytochrome c and formation of the liposomal cytochrome c and nitric oxide complex (cyt c3+-NO). A change in the color of the emulsion from light brown to bright pink and spectrophotometric maxima at the wavelength of 528 and 560 nm suggest that the reaction is complete. Next, the emulsion is filtered through a membrane filter with a pore diameter of 0.2 μm, dosed in 3 ml vials, exposed to intense freezing at a temperature of minus 35° C. and is then subject to lyophilic drying in a lyophilizer (e.g. Martin Christ 2-6D, Germany).

EXAMPLE 2

The finished medicinal product "Lipochrome, Lyophilizate for Preparation of Emulsion for Injection" in vials is dissolved in water to obtain an emulsion with cytochrome c at a concentration of 0.675 mg/ml. Contents of vials are combined in one vessel to obtain 100 ml of the emulsion and are bubbled (purged) for 30 minutes with argon, an inert gas, pre-filtered through a hydrophobic filter with a pore diameter of 0.1 μm to remove atmospheric air. After bubbling of the emulsion, an argon supply line is switched to supply nitric oxide (NO) from a solution tank where metallic copper reacts with 30% nitric acid solution with the release of gaseous nitric oxide (NO). After the reaction vessel, argon, a carrier gas, passes through a vessel with a solution of 5 M sodium hydroxide to remove salt-forming admixtures of nitric oxide (NO) and enters a vessel with the emulsion. Treatment with nitric oxide (NO) is performed until complete reconstitution of liposomal cytochrome c and formation of the liposomal cytochrome c and nitric oxide complex (cyt c3+-NO). A change in the color of the emulsion from light brown to bright pink and spectrophotometric maxima at the wavelength of 528 and 560 nm suggest that the reaction is complete. Next, the emulsion is filtered through a membrane filter with a pore diameter of 0.2 μm, dosed in 3 ml vials, exposed to intense freezing at a temperature of minus 35° C. and is then again subject to lyophilic drying in a lyophilizer (e.g. Martin Christ 2-6D, Germany).

EXAMPLE 3

The nitroso compound S-nitrosoglutathione (GS-NO) is added to 100 ml of the emulsion of the half-product of the medicinal product "Lipochrome, Lyophilizate for Preparation of Emulsion for Injection" to obtain a concentration of 0.01 M and is bubbled (purged) for 30 minutes with argon, an inert gas, pre-filtered through a hydrophobic filter with a pore diameter of 0.1 μm to remove atmospheric air. After bubbling of the emulsion, an argon supply line is switched to supply nitric oxide (NO) from a solution tank where metallic copper reacts with 30% nitric acid solution with the release of gaseous nitric oxide (NO). After the reaction vessel, argon, a carrier gas, passes through a vessel with a solution of 5 M sodium hydroxide to remove salt-forming admixtures of nitric oxide (NO) and enters a vessel with the emulsion. Treatment with nitric oxide (NO) is performed until complete reconstitution of liposomal cytochrome c and formation of the liposomal cytochrome c and nitric oxide complex (cyt c3+-NO). A change in the color of the emulsion from light brown to bright pink and spectrophotometric maxima at the wavelength of 528 and 560 nm suggest that the reaction is complete. Next, the emulsion is filtered through a membrane filter with a pore diameter of 0.2 μm, dosed in 3 ml vials, exposed to intense freezing at a temperature of minus 35° C. and is then subject to lyophilic drying in a lyophilizer (e.g. Martin Christ 2-6D, Germany).

EXAMPLE 4

The nitroso compound S-nitrosoglutathione (GS-NO) is added to 100 ml of the emulsion of the half-product of the medicinal product "Lipochrome, Lyophilizate for Preparation of Emulsion for Injection" to obtain a concentration of 0.1 M. Then follow Example 3 for nitrosylation with nitric oxide (NO) and obtaining a pharmacologically active liposomal agent (target product).

EXAMPLE 5

100 ml of the emulsion of the half-product of the medicinal product "Lipochrome, Lyophilizate for Preparation of Emulsion for Injection" is bubbled (purged) for 30 minutes with argon, an inert gas, pre-filtered through a hydrophobic filter with a pore diameter of 0.1 μm to remove atmospheric air. After bubbling of the emulsion, an argon supply line is switched to supply nitric oxide (NO) from a solution tank where metallic copper reacts with 30% nitric acid solution with the release of gaseous nitric oxide (NO). After the reaction vessel, argon, a carrier gas, passes through a vessel with a solution of 5 M sodium hydroxide to remove salt-forming admixtures of nitric oxide (NO) and enters a vessel with the emulsion. Treatment with nitric oxide (NO) is performed until complete reconstitution of liposomal cytochrome c and formation of the liposomal cytochrome c and nitric oxide complex (cyt c3+-NO). A change in the color of the emulsion from light brown to bright pink and spectrophotometric maxima at the wavelength of 528 and 560 nm suggest that the reaction is complete.

Next, the nitroso compound S-nitrosoglutathione (GS-NO) is added to a concentration of 0.01 M to the emulsion and mixed. Then the emulsion is filtered through a membrane filter with a pore diameter of 0.2 μm, dosed in 3 ml vials, exposed to intense freezing at a temperature of minus 35° C. and is then subject to lyophilic drying in a lyophilizer (e.g. Martin Christ 2-6D, Germany).

EXAMPLE 6

A pharmacologically active liposomal agent (the target product) is obtained in accordance with Example 5 with the only modification: the nitroso compound S-nitrosoglutathione (GS-NO) is added to a concentration of 0.1 M.

In Examples 7-10, the technological processes of the claimed method were performed with S-nitrosocysteine (Cys-NO) in accordance with Examples 3-6.

In examples 11-14, the technological processes of the claimed method were performed with S-nitroso-N-acetylpenicillamine (SNAP) in accordance with Examples 3-6.

In accordance with the object of the invention, the quality of the target product—the liposomal agent containing nitric oxide (NO) was evaluated for pharmaceutical activity in preclinical in vitro studies.

The pharmacological action of the target products obtained by the claimed methods (Examples 1-6) was studied using the following experimental models:
1) contractile activity of rat thoracic aorta segments;
2) contractile activity of strips of cavernous bodies taken from a rat penis.

The experimental results show that, starting with a concentration of $10^{-8}$ mol/l, target products (Examples 1, 2) are able to induce dose-dependent relaxation of intact segments of aorta in rats, though the marked effect was induced by a sample at a concentration of $3 \times 10^{-8}$ mol/l.

When exposed to the liposomal cytochrome c and nitric oxide complex (cyt c3+-NO) at a concentration of $10^{-6}$ mol/l, the maximum amplitude of vasodilation was $(87.8 \pm 2.2)\%$ (n=11). The median effective concentration (EC50) of a sample, expressed as the logarithm of concentration (Log M), was $(-6.8 \pm 0.01)$, (n=11) (FIG. 1). The study of a sample on deendothelized ring aorta segments shows that the contractile activity of deendothelized aorta specimens did not change compared with intact vessels: the maximum amplitude of vasodilation was $(91.4 \pm 2.7)\%$, (n=9), which did not significantly differ from that of control (p>0.05). The analysis of the results shows that the removal of endothelium did not significantly affect the sensitivity of effector elements of vessels exposed to the liposomal cytochrome c and nitric oxide complex (cyt c3+-NO): EC50=$(-6.8 \pm 0.03)$ (n=9; P>0.05) (FIG. 1).

Thus, the experimental results suggest that the removal of an endothelial layer of vessels does not affect the dilatory action of the ex-tempore complex (cyt c3+-NO). This allows us to claim that this sample is characterized by endothelium-independent action.

Figure 2:
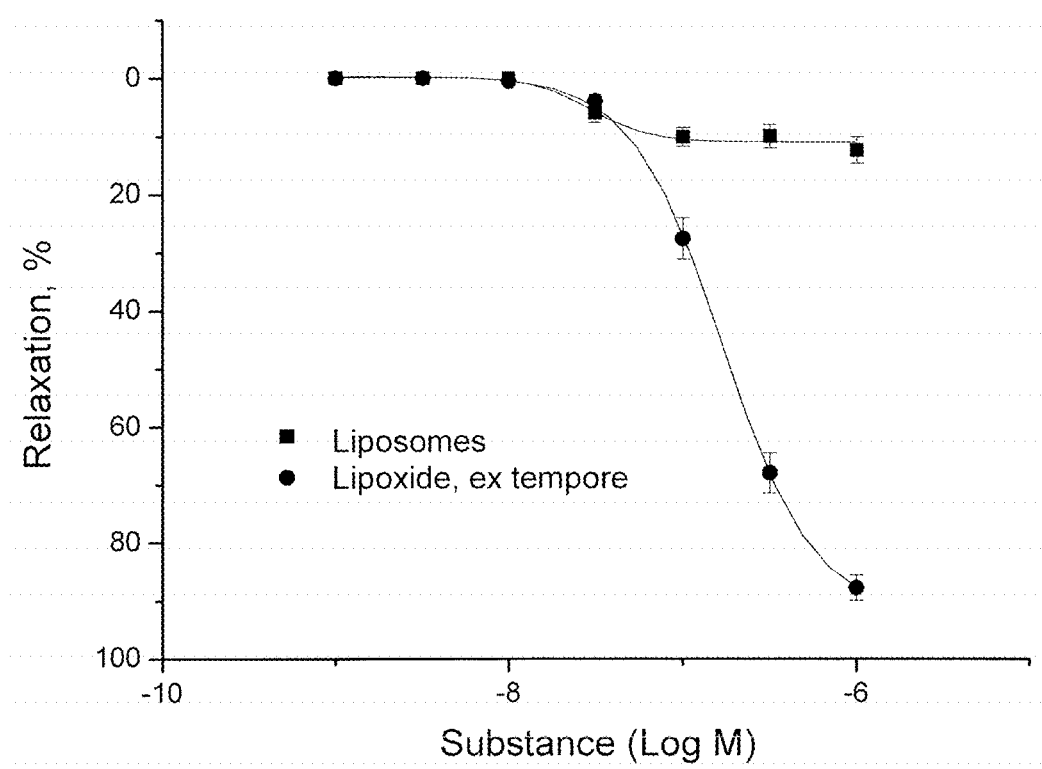
FIG. 2 is a diagram illustrating the comparative efficacy of liposomes acting as an element of the liposomal cytochrome c and nitric oxide complex (Lipoxide) and a sample of the ex-tempore liposomal cytochrome c and nitric oxide complex (Lipoxide) in terms of the contractile activity of rat thoracic aorta segments pre-activated by phenylephrine ($10^{-6}$ mol/l).

To identify a possible contribution of liposomes to the vasodilatory effect of the ex-tempore liposomal cytochrome c and nitric oxide complex (cyt c3+-NO), liposomes were separately tested for their effect on the contractile activity of aorta smooth muscles (SM). The results show that liposomes are able to exhibit a weak dose-dependent vasodilator activity starting with a concentration of $10^{-8}$ mol/l with a maximum effect $(12.3 \pm 2.2\%)$ seen at a concentration ($10^{-6}$ mol/l), which significantly differs from the maximum amplitude of the dilatory response achieved with the ex-tempore liposomal cytochrome c and nitric oxide complex (cyt c3+-NO) (n=8, P≤0.001) (FIG. 2). As shown on FIG. 2, the effect of low concentrations of liposomes does not differ from the overall efficacy of the complex. A significant difference in the efficacy was seen at a concentration of $10^{-7}$ mol/l. At the same time, EC50 $(-7.5 \pm 0.07)$ was significantly different from that of the ex-tempore liposomal cytochrome c and nitric oxide complex (cyt c3+-NO) (n=9; P≤0.05) indicating an increased sensitivity of vascular tissue specimens to the action of liposomes.

Thus, the study results show that liposomes make a significant contribution to the dilatory effect of low concentrations of the ex-tempore liposomal cytochrome c and nitric oxide complex (cyt c3+-NO). It is fair to assume that efficacy of the ex-tempore liposomal cytochrome c and nitric oxide complex (cyt c3+-NO) at low concentrations (up to $10^{-7}$ mol/l) is due to the effect of liposomes. At the same time, liposomes exhibit an insignificant effect on the maximum vasodilation caused by the action of the ex-tempore liposomal cytochrome c and nitric oxide complex (cyt c3+-NO).

Figure 3:
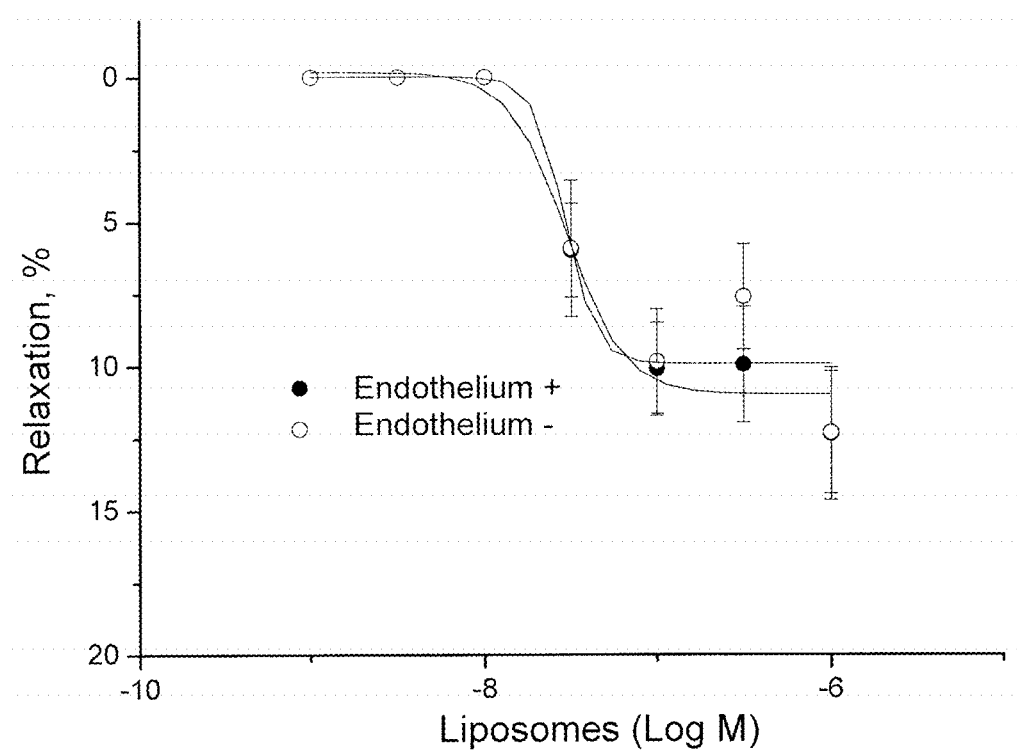
FIG. 3 is a diagram illustrating the contractile activity of intact and deendothelized rat thoracic aorta segments pre-activated by phenylephrine ($10^{-6}$ mol/l) exposed to liposomes.

The testing of liposomes using deendothelized ring aortic segments shows that efficacy of liposomes did not change compared with their effect on intact vessels: the maximum dilatory effect did not significantly differ from the response of intact vessels: (12.3±2.1)%, (n=6, p>0.05). The analysis of the results shows that the removal of the endothelium did not significantly affect sensitivity of effector elements of vessels to the action of the complex: EC50=(−7.5±0.2) (n=6; P>0.05) (FIG. 3).

A study was conducted to compare two samples of the liposomal cytochrome c and nitric oxide complex II (cyt c3+-NO) (Examples 1, 2): a sample prepared several hours before the experiment (ex tempore) and a lyophilized sample, a working solution of which was prepared 5 minutes before testing because previous studies suggest that a sample of the ex-tempore liposomal cytochrome c and nitric oxide (cyt c3+-NO) was characterized by physical and chemical parameters of an unstable compound capable of losing its vasodilatory properties within a rather short period of time under the influence of oxidation.

Figure 4:
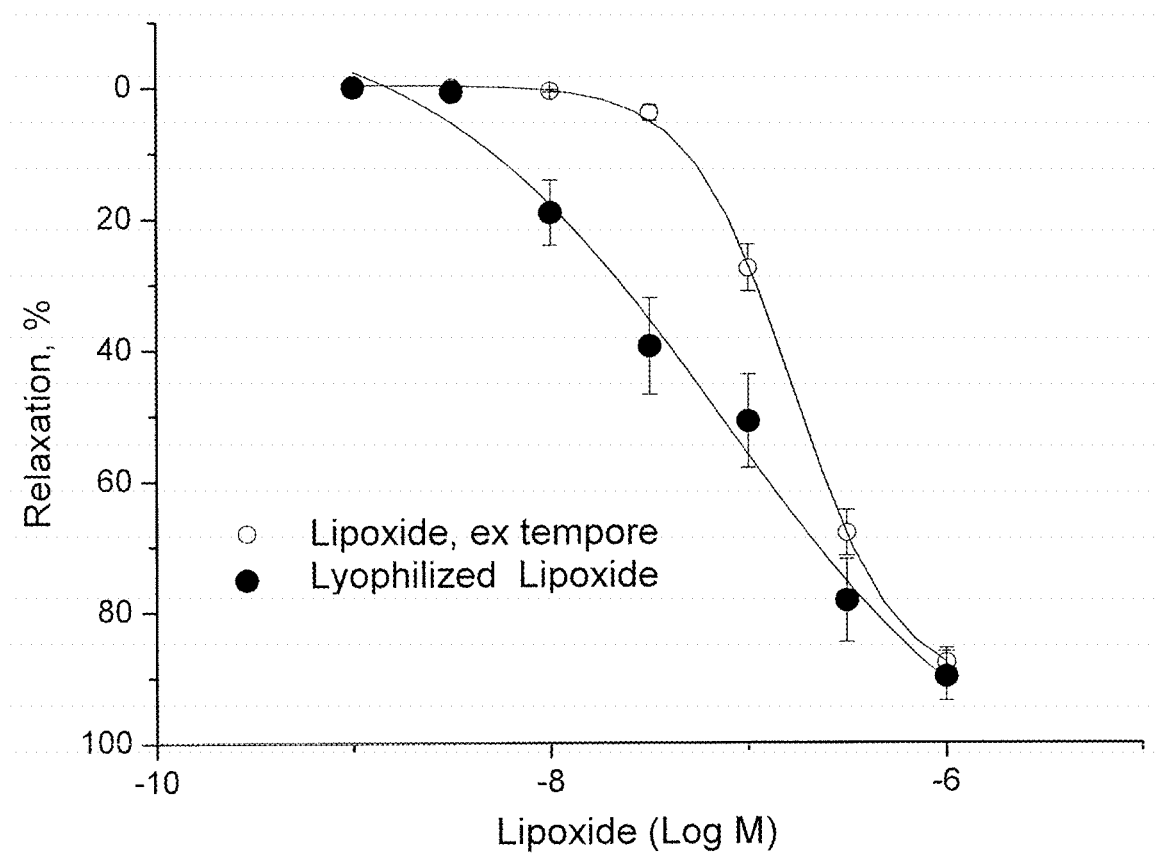
FIG. 4 is a diagram showing the comparative efficacy of samples of the ex-tempore liposomal cytochrome c and nitricoxide complex (Lipoxide) and lyophilized liposomal cytochrome c and nitric oxide complex (Lipoxide) in terms of the contractile activity of rat thoracic aorta segments pre-activated by phenylephrine ($10^{-6}$ mol/l).

The study results show that the lyophilized liposomal cytochrome c and nitric oxide complex (cyt c3+-NO) also induced an effective dose-dependent dilation of intact specimens of rat aorta smooth muscle (SM) with a maximum effect (89.9±3.8)% seen at a concentration of ($10^{-6}$ mol/l), which did not significantly differ from the maximum relaxation seen in response to a sample of the ex-tempore liposomal cytochrome c and nitric oxide (cyt c3+-NO) (n=7, P>0.05) (FIG. 4). However, the analysis of EC50 values revealed significant differences in the action of the lyophilized liposomal cytochrome c and nitric oxide complex (cyt c3+-NO): the latter had EC50 of (−7.1±0.03) (n=7; P≤0.05), which was significantly different from that of the ex-tempore liposomal cytochrome c and nitric oxide (cyt c3+-NO) (FIG. 4). The left shift of the dose-effect curve that is characterized by EC50 is an indicator of increased sensitivity of vascular tissue specimens to the action of the lyophilized sample compared to the ex-tempore sample.

Thus, according to the study results, the lyophilized liposomal cytochrome c and nitric oxide complex (cyt c3+-NO) (Examples 1, 2) has superior efficacy compared with that of the ex-tempore liposomal cytochrome c and nitric oxide complex (cyt c3+-NO), since it exhibits more pronounced efficacy at low concentrations, though the samples do not differ in terms of their maximum effect. It is fair to assume that the higher efficacy of the lyophilized complex is due to the fact that its working solution was prepared immediately before testing and, as such, was less exposed to oxidation processes.

The liposomal cytochrome c and nitric oxide complex (cyt c3+-NO) was found to be an unstable substance capable of oxidizing quickly and losing its dilatory activity (Table 1).

Figure 5:
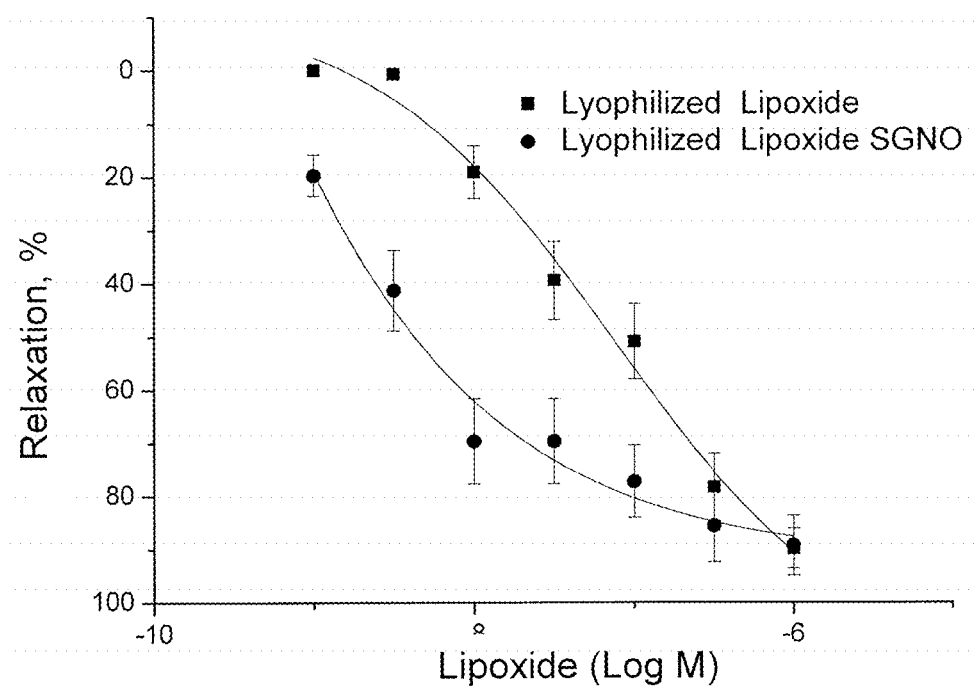
FIG. 5 is a diagram illustrating the comparative efficacy of samples of lyophilized liposomal cytochrome c and nitric oxide complex (Lipoxide) and liposomal cytochrome c and nitric oxide complex with the addition of S-nitrosoglutathione (Lipoxide GSNO) in terms of the contractile activity of rat thoracic aorta segments pre-activated by phenylephrine ($10^{-6}$ mol/l).
Figure 6:
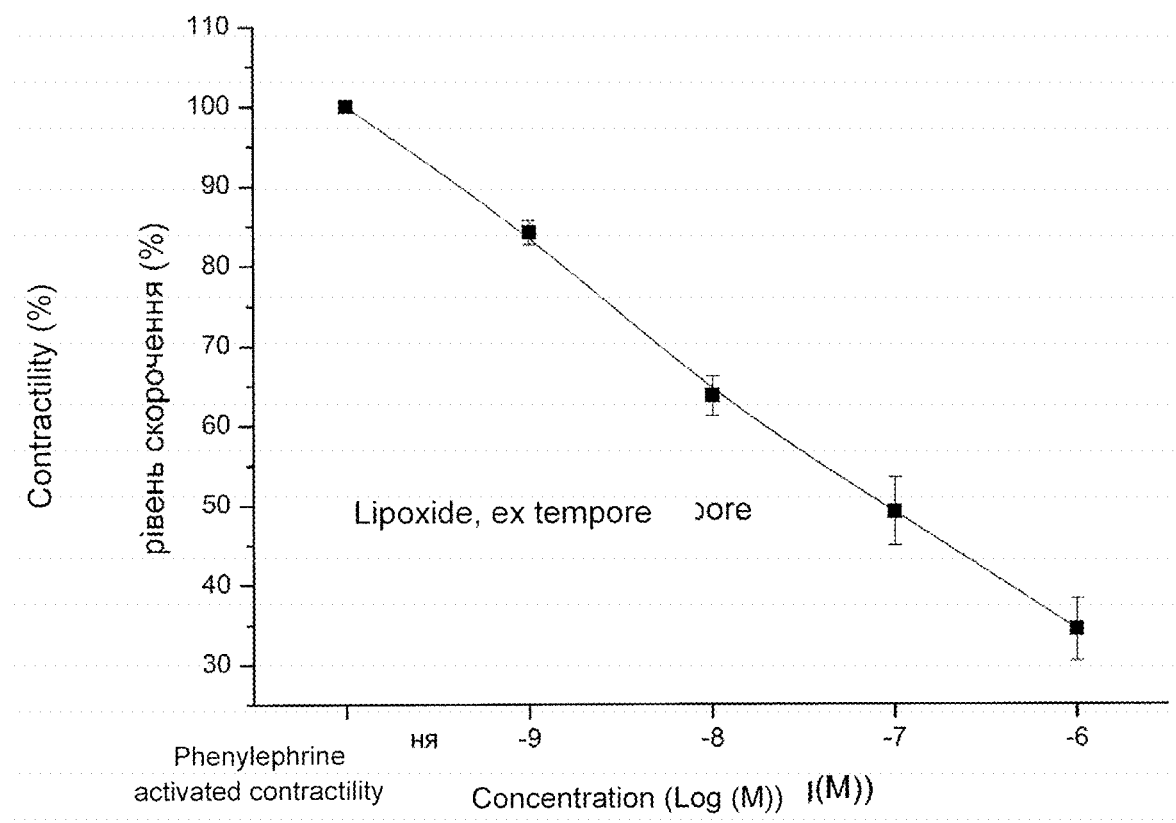
FIG. 6 is a diagram illustrating the relaxing effect of the ex-tempore liposomal cytochrome c and nitric oxide complex (Lipoxide) on cavernous bodies taken from a rat penis pre-stimulated with phenylephrine $10^{-6}$ M.
Figure 7:
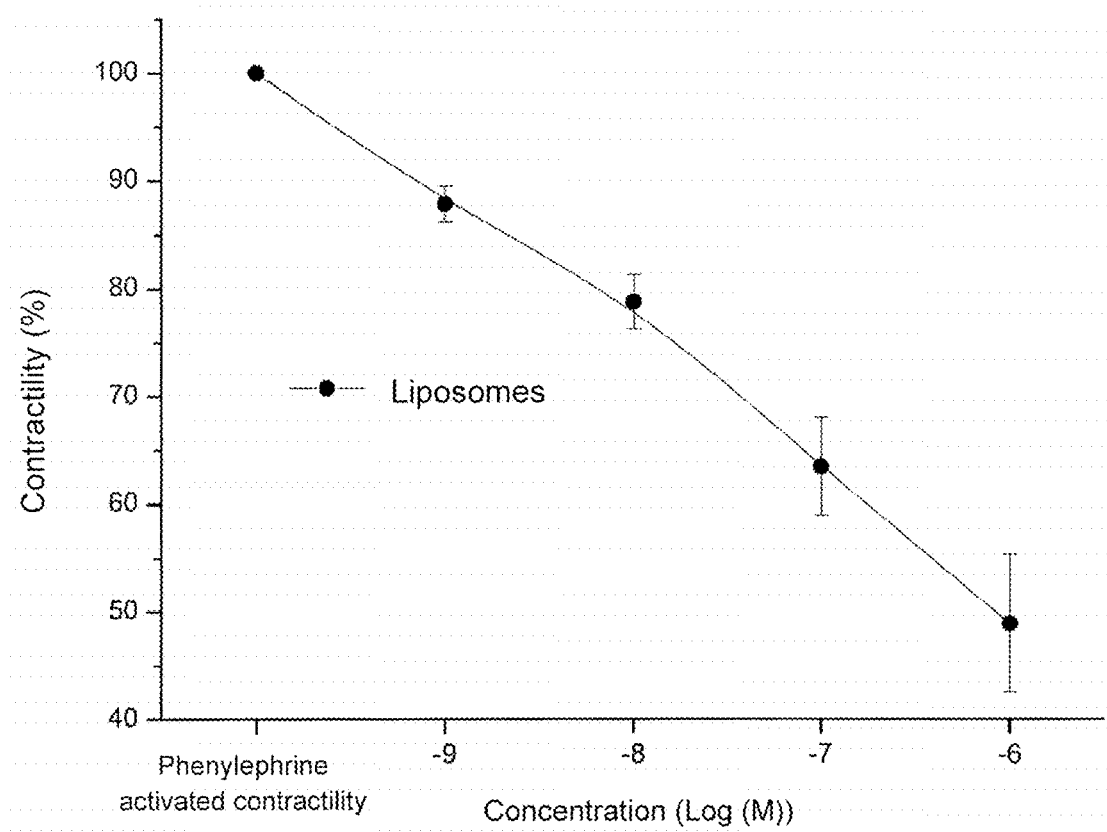
FIG. 7 is a diagram illustrating the comparative effect of liposomes on cavernous bodies taken from a rat penis pre-stimulated with phenylephrine $10^{-6}$ M.
Figure 8:
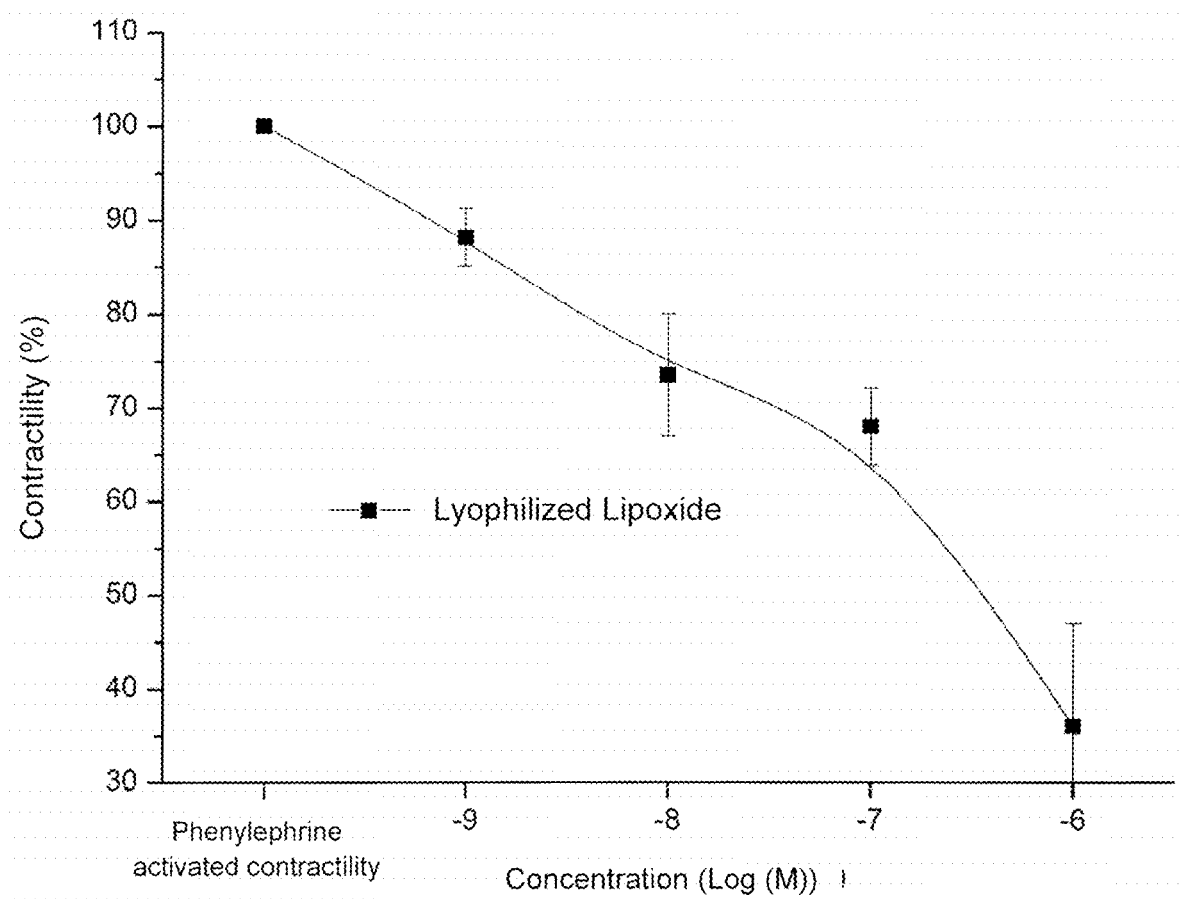
FIG. 8 is a diagram illustrating the relaxing effect of the lyophilized cytochrome c and nitric oxide complex (Lipoxide) on cavernous bodies taken from a rat penis pre-stimulated with phenylephrine $10^{-6}$ M.
Figure 9:
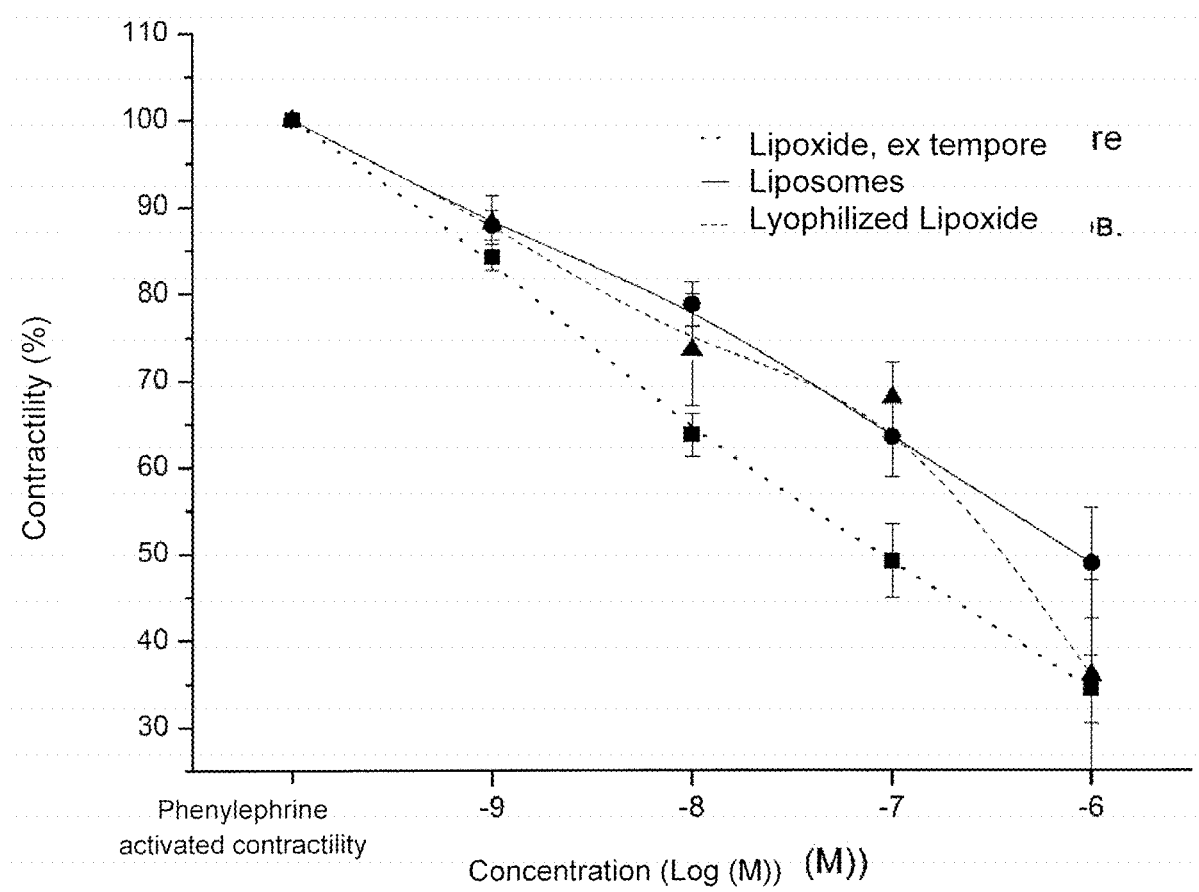
FIG. 9 is a diagram illustrating the comparative effect of liposomes and liposomal cytochrome c and nitric oxide complexes (Lipoxide) on cavernous bodies taken from a rat penis pre-stimulated with phenylephrine $10^{-6}$ M.
Figure 10:
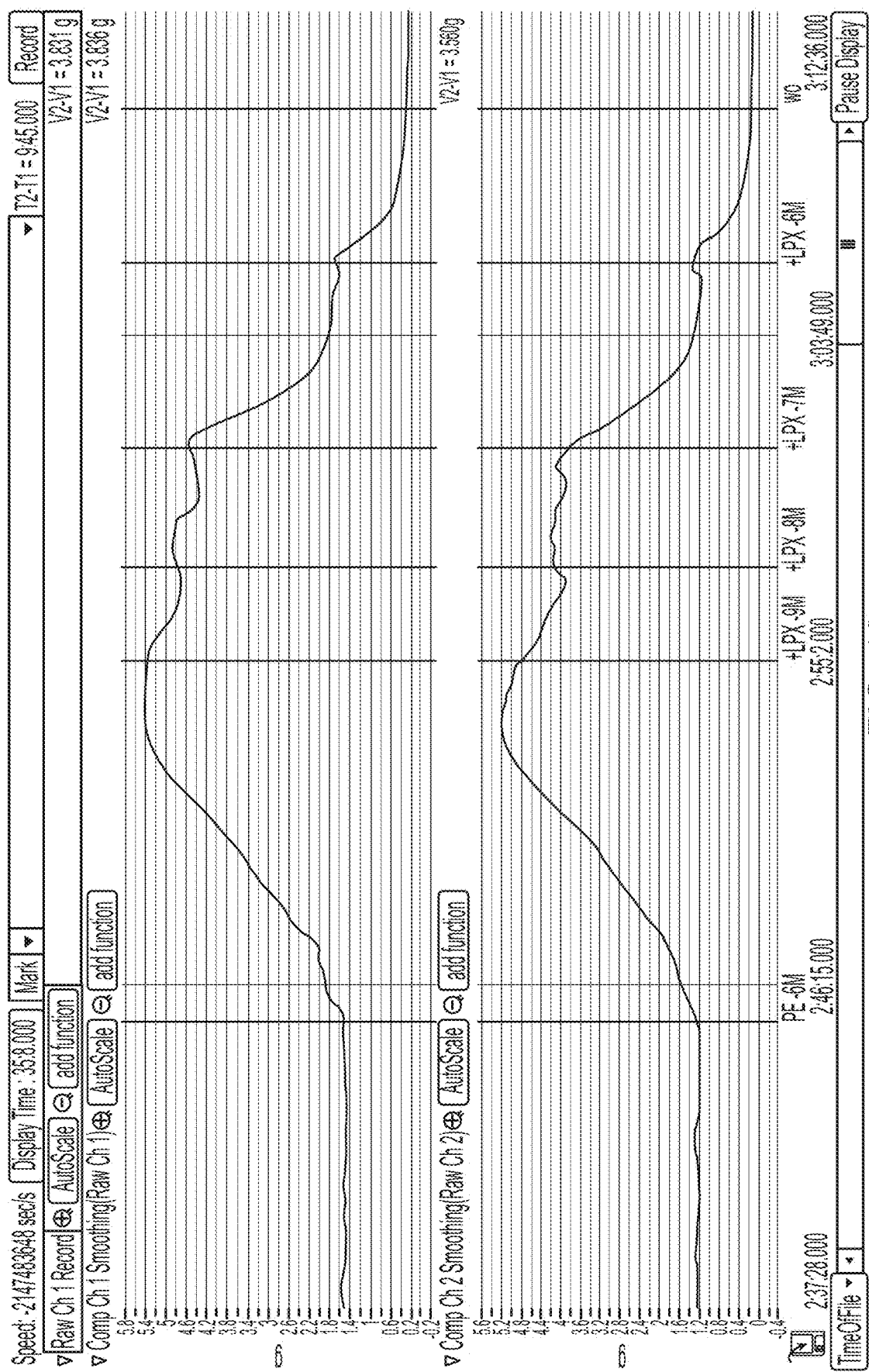
FIG. 10 is a diagram illustrating the original record of the experiment to study the effects of the liposomal cytochrome c and nitric oxide complex with the addition of S-nitrosoglutathione (Lipoxide GSNO) on strips of cavernous bodies taken from a human penis pre-stimulated with phenylephrine $10^{-6}$ M.

However, the lyophilized liposomal cytochrome c and nitric oxide complex (cyt c3+-NO) exhibited greater efficacy than the ex-tempore liposomal cytochrome c and nitric oxide complex (cyt c3+-NO). Therefore, the lyophilized liposomal cytochrome c and nitric oxide (cyt c3+-NO) were modified by synthesized glutathione to get a complex with stable properties (Examples 3-6). Studies have been conducted to determine its efficacy compared to the lyophilized liposomal cytochrome c and nitric oxide complex (cyt c3+-NO). The preliminary results suggest that the complex of liposomal cytochrome and nitric oxide with nitrosoglutathione (cyt c3+-NO−GS-NO) is able to induce a dose-dependent dilatory response in vascular tissue specimens apparently seen at lower concentrations than vasodilation induced by unmodified lyophilized liposomal cytochrome c and nitric oxide complex (cyt c3+-NO) (FIG. 5). At the same time, the maximum vasodilation response did not change significantly: (89.3±5.7)%, (n=3, P>0.05).

An additional study of the target products of the complex (Examples 1-6) used cavernous bodies taken from rats, i.e. syncytia of smooth muscle cells and endothelium located on the stroma of the connective tissue, as an object of research.

After rats were euthanatized in accordance with the recommendations of the European Convention for the Protection of Animals, the penis was quickly dissected and immediately placed in a 20 ml preparative bath with the Krebs solution. Cavernous bodies were released from the connective tissue under microscopic control. Next, a few longitudinal strips of SM syncytia were taken from cavernous bodies and placed in the flow chamber between hooks of the strain gauge and the device for the preliminary (0.3-0.4 g) stretching. After preliminary treatment (for 30-40 minutes) and "pumping" with a solution with an increased (60 mM) KCl content, the strips were subject to pre-contraction with the phenylephrine solution ($10^{-6}$ M) and used in experiments with the test substances.

Experimental data was recorded using the analog-digital converter LabTrax-4/16 and the software application LabScribe2. Given that stimulation with phenylephrine resulted in a significant autorhythmic activity, an adequate evaluation of the results was almost impossible. As a result of thorough digital filtration and the use of data-smoothing methods (using a moving average or the Savitzky-Golay filter based on polynomial approximation of peaks), the data became quite appropriate for further processing. The final data was downloaded to the OriginLab software for processing and graphic design.

The results so obtained are presented in Table 3 below and on FIG. 6-10.

TABLE 3

Relative relaxation of strips of cavernous bodies taken from a rat penis pre-stimulated with phenylephrine $10^{-6}$ M induced by study substances.

| Concentration, log (mol/l) | Liposomal cytochrome c (cyt c3 +− NO), emulsion | | Liposomes (control) | | Liposomal cytochrome c (cyt c3 +− NO), lyophilized | |
|---|---|---|---|---|---|---|
| | Relative contractility, % | Mean-square deviation | Relative contractility, % | Mean-square deviation | Relative contractility, % | Mean-square deviation |
| PhE-6 | 100 | | 100 | | 100 | |
| Lipo-9 | 84.23 | 7.59 | 87.85 | 8.28 | 88.14 | 3.10 |
| Lipo-8 | 63.73 | 12.14 | 78.77 | 12.75 | 73.52 | 6.45 |
| Lipo-7 | 49.18 | 21.47 | 63.49 | 22.79 | 68.00 | 4.13 |
| Lipo-6 | 34.41 | 19.68 | 48.91 | 31.97 | 36.04 | 10.94 |

In recent studies, strips of cavernous bodies taken from a human penis were used as an object of research. Original curves (see, for example, FIG. 10) allow us to observe how the liposomal cytochrome c and nitric oxide complex with the addition of S-nitrosoglutathione (Lipoxide GSNO) is able to induce a pronounced relaxation of smooth muscles. At the same time, it should be noted that the relaxation begins with very low concentrations.

CITED REFERENCES

1. A. N. Osipov, G. G. Borisenko, Yu. A. Vladimirov "Biological role of nitrosyl complexes of hemoproteins", Uspekhi biologicheskoi khimii, vol. 47, 2007, p. 259-292.
2. Vanin, A. F., Mordvintcev, P. I., Hauschildt, S., and Mulsch, A. (1993) Biochim. Biophys. Acta, 1177, 37-42.
3. Vanin, A. F. (1991) FEBS Lett., 289, 1-3.
4. Mulsch, A., Mordvintcev, P. I., Vanin, A. F., and Busse, R. (1991) FEBS, Lett. 294, 252-256.
5. Stone, J. R., Sands, R. H., Dunham, W. R., and Marletta, M. A. (1995) Biochem. Biophys. Res. Commun., 207, 572-575.
6. Zhang, F., White, J. G., and Iadecola, C. (1994) J. Cereb. blood flow metab., 14, 217-226.
7. Frostell, C., Fratacci, M., and Wain, J. C. (1991) Circilation, 83, 2038-2047.
8. Gaston, B., Reilly, J., and Drazen, J. M. (1993) Proc. Natl. Acad. Sci. USA, 90, 10957-10961.
9. Koshland, D. E., and Culotta, E. (1992) Science, 258, 1862-1865.
10. Beckman, J. S., Beckman, T. W., Chen, J., and Marshall, P. A. (1990) Proc. Natl. Acad. Sci. USA, 87, 1620-1624.
11. Bredt, D. S., Hwang, P. M., and Lowenstein, C. (1991) Nature, 351, 714-718.
12. Stuehr, D. J., and Ikeda, S. M. (1992), J. Biol. Chem., 267, 20547-20550.
13. Brown, G. C. (1997) Mol. Cell. Biochem., 174, 189-192.
14. Заявка EP 3 158 990 A1, опублікована 26 Apr. 2017.
15. Swati Basu, Agnes Keszler, Natalia A. Azaroval, Nneka Nwanzel, Andreas Perlegas, Sruti Shiva, Katarzyna A. Broniowska, Neil Hogg, Daniel B. Kim-Shapiro, A Novel Role for Cytochrome c: Efficient Catalysis of SNitrosothiol Formation, Free Radic Biol Med. (2010 Jan. 15); 48(2): 255. doi:10.1016/j.freeradbiomed.2009.10.049.
16. Sharpe, M. A., and Cooper, C. E. (1998) Biochem. J., 332, 9-19.
17. Patent UA 44318 for utility model "Method for obtaining liposomal cytochrome C", A61K 9/00, published Sep. 25, 2009.
18. Patent RU 2110990 for the invention "Liposomal vesicle with Cytochrome C", A61K9/127, published May 20, 1998.
19. Application CN 101019836 for the invention «Nanometer cytochrome liposome medicine and its preparation», A61K38/06; A61K38/17; A61K47/24; A61K47/34; A61K47/42; A61K9/127; A61K9/19; A61P39/02; A61P43/00, published Aug. 22, 2007.
20. Application EA201201592 for the invention «Method for obtaining a liposomal form of cytochrome C», A61K38/00; A61K47/44; A61K9/127; A61P27/02, published Jun. 30, 2014.

The invention claimed is:

1. A method of obtaining a pharmacologically active liposomal cytochrome c and nitric oxide complex, the method comprising treating a liposomal cytochrome c emulsion with gaseous nitric oxide (NO) until liposomal cytochrome c is completely reconstituted and adding an S-nitroso compound to the liposomal cytochrome c emulsion.

2. The method according to claim 1, wherein the liposomal cytochrome c emulsion is treated by supplying gaseous nitric oxide (NO) using an inert carrier gas.

3. The method according to claim 2, wherein the inert carrier gas is argon.

4. The method according to claim 2, wherein the inert carrier gas is pre-filtered to a purity of at least 99.995%.

5. The method according to claim 2, wherein the inert carrier gas is purified from salt-forming admixtures of nitric oxide (NO) after contact with gaseous nitric oxide (NO).

6. The method according to claim 2, wherein the liposomal cytochrome c emulsion is obtained by high-pressure homogenization followed by lyophilic drying to produce a lyophilizate.

7. The method according to claim 6, wherein the liposomal cytochrome c emulsion is reconstituted from the lyophilizate.

8. The method according to claim 1, wherein liposomal cytochrome c having the form of emulsion is pre-filtered using hydrophilic membranes before gaseous nitric oxide (NO) is supplied.

9. The method according to claim 8, wherein prefiltration is performed through at least two successively positioned hydrophilic membranes with a gradually decreasing pore diameter.

10. The method according to claim 1, wherein liposomal cytochrome c having the form of emulsion is treated with gaseous nitric oxide (NO) at a room temperature.

11. The method according to claim 1, wherein the emulsion is subject to additional filtration after the reconstitution of liposomal cytochrome.

12. The method according to claim 11, wherein, after the additional filtration, the emulsion is frozen at a temperature of minus 35° C. followed by lyophilic drying.

13. The method according to claim 1, wherein an S-nitroso compound is added to the emulsion to obtain a concentration in the range of 0.01 to 0.1 M in the emulsion.

14. The method according to claim 1, wherein an S-nitroso compound is added to the emulsion before the treatment with gaseous nitric oxide (NO) and/or during the treatment with gaseous nitric oxide (NO) and/or after the treatment with gaseous nitric oxide (NO).

15. The method according to claim 1, wherein an S-nitroso compound is selected from a group of S-nitrosothiols consisting of nitroso-N-acetylpenicillamine, S-nitrosoglutathione (GS-NO), S-nitrosocysteine (Cys-NO), and any mixture thereof.

* * * * *